United States Patent [19]

Tanaka et al.

[11] Patent Number: 5,470,563
[45] Date of Patent: Nov. 28, 1995

[54] ALLEVIATING SKIN IRRITATION RESULTING FROM APPLYING TACKY TAPES

[75] Inventors: Hiroshi Tanaka; Toshiaki Kobayashi; Tomiyuki Nanba; Masaaki Ishiwatari; Toshio Yoneyama; Kimio Ohno; Takashi Matsumoto; Tetsuya Kanbe; Takashi Isa; Yoshiyuki Ogusu, all of Yokohama, Japan

[73] Assignee: Shiseido Company Ltd., Tokyo, Japan

[21] Appl. No.: 442,376

[22] Filed: Nov. 28, 1989

Related U.S. Application Data

[63] Continuation of Ser. No. 107,128, Oct. 9, 1987, abandoned.

[30] Foreign Application Priority Data

Nov. 6, 1986 [JP] Japan .................. 61-264725
Nov. 6, 1986 [JP] Japan .................. 61-264726
Nov. 7, 1986 [JP] Japan .................. 61-265307
Feb. 4, 1987 [JP] Japan .................. 62-24380

[51] Int. Cl.$^6$ .................. A61K 7/032; A61K 7/135; A61K 7/155; A61K 9/70; A61K 47/34; A61L 15/58; A61L 15/26; C08J 11/08
[52] U.S. Cl. .................. 424/448; 424/449; 424/62; 424/63; 424/DIG. 3; 427/2.31; 602/52; 602/54; 525/100
[58] Field of Search .................. 424/443, 444, 424/445, 446, 447, 448, 449; 528/14

[56] References Cited

U.S. PATENT DOCUMENTS

| 4,151,319 | 4/1979 | Sackoff et al. ............... 428/40 |
| 4,826,946 | 5/1989 | Eichenauer et al. .......... 528/14 |
| 4,867,981 | 9/1989 | Grof ................................ 424/443 |

FOREIGN PATENT DOCUMENTS

| 60-126209 | 7/1985 | Japan . |
| 60-197610 | 10/1985 | Japan . |
| 60-228405 | 11/1985 | Japan . |
| 1453383 | 9/1974 | United Kingdom ............ C08L 83/12 |

OTHER PUBLICATIONS

Copy of partial English Translation of: Yuki Gosei Kagaku, vol. 40, No. 6, 1982 (3 pgs. of trans.).

*Primary Examiner*—Edward J. Webman
*Attorney, Agent, or Firm*—Sprung Horn Kramer & Woods

[57] ABSTRACT

A skin irritation alleviation agent composed of a polyoxyalkylene-modified organopolysiloxane is provided. Various compositions including skin external application compositions, cosmetic or similar compositions (e.g., an adhesive composition for a false eyelash, a decolorant composition, a depilatory composition, and an eyeliner composition) containing a polyoxyalkylene-modified organosiloxane are also provided. This alleviation agent has a low skin irritation effect and extremely high safety factor when used on the human body.

4 Claims, No Drawings 5,470,563

ALLEVIATING SKIN IRRITATION RESULTING FROM APPLYING TACKY TAPES

This is a continuation of application Ser. No. 07/107,128, filed Oct. 9, 1987 abandoned.

BACKGROUND OF THE INVENTION

1. Field of the Invention

The present invention relates to a skin irritation alleviation agent (i.e., "alleviator") and a composition containing the same. More specifically, the present invention relates to a skin external application composition or a cosmetic or similar composition containing a polyoxyalkylene-modified organopolysiloxane, as an alleviator, having a low skin irritation effect and an extremely high safety factor when used on the human body.

2. Description of the Related Art

A surfactant is indispensable as, for example, a solubilizing agent, emulsifier or dispersing agent for dissolving, for example, perfume components in an aqueous system, homogeneously mixing oil components and aqueous components, or dispersing pigments into water or oil components. However, surfactants generally cause a strong skin irritation effect. Accordingly, the surfactant formulated in cosmetics is generally used in a minimum necessary amount.

Surfactants are used in various compositions and products. For example, a tacky tape or sheet for skin external use (e.g., a tacky tape or sheet for patch tests, a tacky tape or sheet for medical or submedical use) has been widely used for medical purposes, but since it is adhered to the skin for a long time, it is well known to cause a skin irritation effect, namely, sticking plaster eruption.

Sticking plaster eruption is now widely known as a contact dermatitis, and the cause for skin irritation thereof is considered to be greatly dependent on the adhesive force of the tape or sheet or the components of the tape or sheet, and on the influences of the stabilizer or accelerator for emulsion polymerization monomers. Moreover, that from the stabilizer of the colloid for storage, and the like cannot be disregarded.

False eyelashes have been widely used in order to make the eyelashes appear longer and denser and add an attractiveness to the eyes. To adhere a false eyelash to the eyelid, an adhesive adopted for false eyelashes has been employed, and from the viewpoint of use characteristics such as adhesive force and ease of removal, a natural or synthetic latex or a synthetic emulsion has been used as the adhesive component.

However, to retain a false eyelash for a long time, the adhesive force must be fairly strong, and for this reason, partly because of the use of the eyelid, which is sensitive, a problem arises in that skin irritation may occur if a person has a sensitive skin, and the like.

A further example is a decolorant usually comprises a first agent having one or two or more alkali agents selected from alkanolamines such as monoethanolamine, diethanolamine, triethanolamine and the like, ammonia, sodium hydroxide, potassium hydroxide, formulated optionally further together with ammonium salts, sodium salts, potassium salts with acids such as carbonic acid, bicarbonic acid, phosphoric acid, citric acid, nitric acid, hydrochloric acid and the like, as the main component, and a second agent comprising an oxidizing agent (generally hydrogen peroxide) as the main component. During use, the first agent and second agent are mixed and applied by a brush onto head hair or unnecessary hair to be decolored on arms or legs, left to stand for about 10 to 30 minutes, and then washed away. The mixing ratio of the first agent and the second agent may be an approximate ratio depending on the purpose, but the ratio generally employed is the first agent:the second agent =1:1 to 1:5.

Also, to obtain a sufficient decoloration power, the alkali agent is adjusted during mixing of the first agent and the second agent so that the pH is generally 9 to 12, and hydrogen peroxide is formulated to an amount of 1 to 5% by weight during mixing. Further, during coating of the hair or unnecessary hair on arms or legs, to enable an easy coating or to prevent dripping of the liquid, the liquid must be appropriately viscous, and therefore, is in a gel-like or cream-like form. For this purpose, a surfactant is used. A surfactant has the actions of a gelling agent, emulsifying agent or dispersing agent, and solubilizing agent, but generally causes the problem of skin irritation. The above respective irritations are augumented synergetically when a decolorant containing an alkali and hydrogen peroxide having a strong skin irritation effect is formulated with a surfactant, whereby rubor, eruption or even sometimes edema may occur, with pain to the user, thus posing a serious problem for the health and appearance of the skin.

Yet another example is that of depilatories in the form of a wax, cream, liquid or tacky tape are generally utilized. However, most of these depilatories have dermatological safety problems, different from conventional external dermatological preparations. For example, in the case of a depilatory wax, the wax is generally heated to a temperature higher than the melting point to make it liquid, then the skin to be depilated is coated with the melted wax, and upon solidification, the solidified wax is peeled off together with the hair. Thus, this is a depilatory utilizing a physical action, and the base used therefor is rosin (pine resin), which is primarily composed of abietic acids, which cause irritation considered to be due to the impurities contained therein, whereby the coated skin sometimes is covered with red swellings or blisters. Also, a depilatory cream or depilatory liquid comprises an S—S bond cleaving agent for the keratin structure of hair formulated in a liquid base, for which a thioglycolic acid is generally used. However, many of the S—S bond cleaving agents have serious skin irritation effects and skin safety problems. Similarly, in the case of a tacky tape or sheet, skin eruptions will frequently occur, which may be considered to be caused by the components in the tacky layer.

Another example is an eyeliner used to make the eyes more impressive and attractive. An eyeliner is frequently formulated with a synthetic resin emulsion capable of forming an oil-resistant, water resistant film, for cosmetic preservation, to prevent a makeup breakdown by skin fat or foundation or the oil or fat contained in an eyeshadow, or a makeup breakdown caused by sweat or tears. However, to maintain the cosmetic effect for a long period, the film formed must be relatively firm, and thus, partly because of the very sensitive tissue at the edge of the eye, a problem arises in that skin irritation may occur if a person has sensitive skin and the like.

SUMMARY OF THE INVENTION

Accordingly, the objects of the present invention are to eliminate the above-mentioned disadvantages of the prior art and to provide a skin irritation alleviation agent (i.e., "alleviator").

Another object of the present invention is to provide skin external application compositions or cosmetic or similar compositions or products, including a tacky tape or sheet for skin external use, an adhesive composition for a false eyelash, a decolorant composition, a depilatory composition, and an eyeliner composition, having a low skin irritation effect and extremely high safety factor when used on the human body, without impairing the intended purpose thereof.

Other objects and advantages of the present invention will be apparent from the following description.

In accordance with the present invention, there is provided a skin irritation alleviation agent comprising a polyoxyalkylene-modified organopolysiloxane having the formula (A), (B), (C), or (D).

Tacky Tape or Sheet

The present inventors have found that sticking plaster eruption caused by a tacky tape or sheet can be remarkably alleviated by formulating a specific compound of the organopolysiloxane type in a tacky layer, and the present invention was accomplished on the basis of this finding.

In accordance with the present invention, there is also provided a tacky tape or sheet for skin external application use comprising a polyoxyalkylene-modified organopolysiloxane having the above-mentioned formula (A), (B), (C), or (D) in a tacky layer.

The polyoxyalkylene-modified organopolysiloxane used in the present tacky tape or sheet preferably contains 2 to 80% by weight, preferably 11 to 50% by weight of a polyoxyalkylene group. Also, the polyoxyalkylene-modified organopolysiloxane preferably has an average molecular weight of 3000 or more, more preferably 5000 to 50000. The

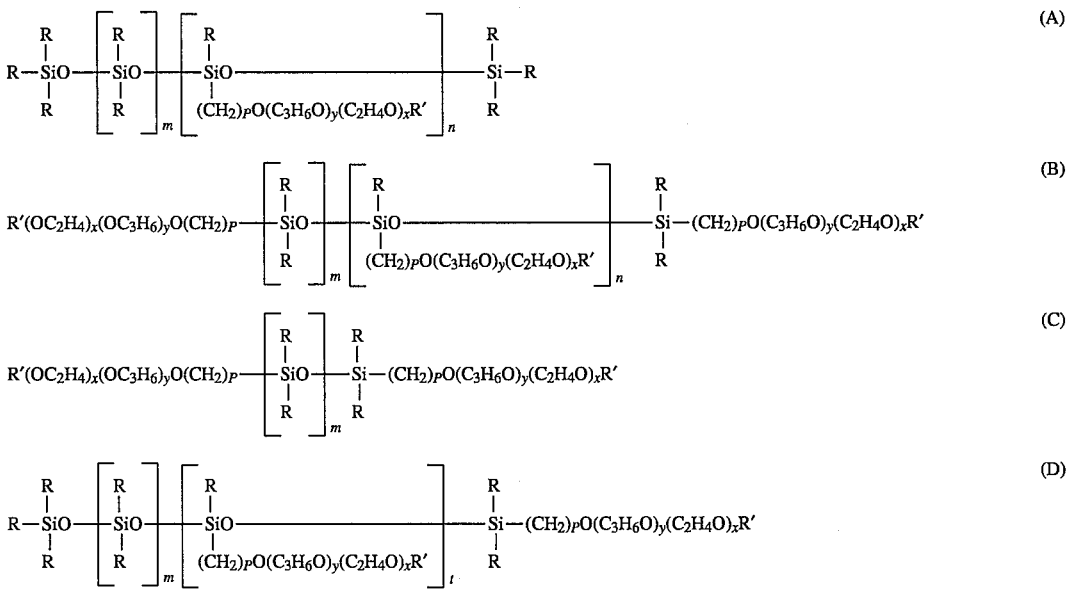

wherein, R is an alkyl having 1 to 3 carbon atoms or phenyl, R' is hydrogen or an alkyl group having 1 to 12 carbon atoms, p is an integer of 1 to 5, m is an integer of 5 to 100, n and x are each an integer of 1 to 50, and t and y are each an integer of 0 to 50.

DESCRIPTION OF THE PREFERRED EMBODIMENTS

Skin Irritation Alleviator

The alleviator of the present invention having the formula (A), (B), (C), or (D) can be prepared by a method known in the art. For example, to obtain a desired molecular weight, the alleviator of the present invention can be prepared by a suitable selection of the amount of the alkylene oxide charged and the polymerization degree of the mother nucleus —SiO ($R^2$)—.

The alleviator of the present invention can be used in the preparation of, for example, tacky tapes or sheets for skin external application, basic cosmetics, make-up cosmetics, hair cosmetics, and detergents.

The alleviator of the present invention is a compound having a remarkably low skin irritation effect, particularly a compound which reduces the skin irritation effect of the oil component when mixed with an oil component, and the like.

amount formulated is preferably 0.1% to 90% by weight, more preferably 0.1% to 50% by weight, based on the total amount of the tacky layer.

Furthermore, according to the present invention, carboxyvinyl polymer can be preferably formulated into the tacky layer of the tape or sheet to improve the tackiness of the tape or sheet to the skin and to increase the retention force thereof to the skin. The carboxyvinyl polymer is advantageously used in the form of an aqueous solution to be uniformly dispersed in the tacky layer. The preferable amount formulated is 1% to 5% by weight, based on the total amount of the tacky layer. Examples of the carboxyvinyl polymer are Carbopol® (Goodrich Co.) and Hiviswako® (Wako Pure Chemical Industries Ltd.).

The tape or sheet containing a polyoxyalkylene-modified organopolysiloxane according to the present invention is a tacky tape or sheet having no skin irritation effect, an extremely high safety factor when used on the human body, and a good adhesiveness, and therefore, is of an extremely high industrial value.

According to the present invention, various additives such as drugs, dissolution and/or diffusion improvers, humectants, keratin or cuticle softening agents, and percutaneous absorption accelerators can be formulated, in addition to the above-mentioned essential constituents, into the organopolysiloxane layer. Typical examples of such drugs are as follows:

Analgesic and Antiphlogistic:

Salicylic acid, methyl salicylate, glycol salicylate, 1-menthol, camphor, nonylic vanilyl amide, tocopherol, mentha oil, thymol, capsicum extract, powdered capsicum, tocopherol acetate, dl-camphor, acetaminophen, mefenamic acid, flufenamic acid, indomethacin, diclofenac sodium, alclofenac, oxyphenbutazone, phenylbutazone, ibuprofen, and flurbiprofen;

Antimicrobial:

Nitrofurazone, nystatin, sulfacetamide, clotrimazole, and pentamycin;

Antibiotic:

β-Lactam, penicillin, cephalosporin, oxytetracycline, fradiomycin sulfate, erythromycin, and chloramphenicol;

Vitamin:

Ergocalciferol, cholecalciferol, and riboflavin butyrate;

Vasodilator:

Nitroglycerin, nifedipine, isosorbide dinitrate, erythritol tetranitrate, and pentaerythritol tetranitrate;

Antihistaminic:

Diphenhydramine hydrochloride, chlorpheniramine, and diphenylimidazole;

Corticosteroid:

Hydrocortisone, prednisolone, paramethasone, betamethasone, beclomethasone dipropionate, dexamethasone, triamcinolone, triamcinolone acetonide, fluocinolone, fluocinolone acetonide and fluocinolone acetonide acetate;

Hypnotic:

Phenobarbital, amobarbital, and cyclobarbital;

Tranquillizers:

Fluphenazine, thioridazine, benzodiazepine, diazepam, lorazepam, flunitrazepam, and chlorpromazine;

Antihypertensive drugs:

Clonidine, callicrein, hydrothiazide, and bendroflumethiazide;

Anesthetic:

Lidocaine and ethyl aminobenzoate;

Antiepileptic:

Nitrazepam and meprobamate.

Examples of other additives are percutaneous absorption accelerators such as dimethyl sulfoxide, dodecyl sulfoxide, methyloctyl sulfoxide, dimethyldecyl phosoxide, diethylacetamide, N-hydroxyethyllactamide, dimethylacetamide, N,N-dimethyldodecamide, dimethylformamide, methylbenzoic acid diethylamide, tetrahydrofurfuryl alcohol, tetrahydrofuran, sorbitol, dodecylpyrolidone, methylpyrolidone, urea, diethyladipate, squalene, squalane, acetylated lanolin, cetyl lactate, dioctylsebacate, ethoxystearyl alcohol, lanolic lanolin alcohol, fatty acid alcohol, salicylic acid, stilisooctanoate, liquid paraffin, vaseline, amino acid, proteolytic enzymes, ethyl nicotinate, 1-menthol, fatty acid triglyceride, polyoxyalkylene glycol, fatty acid mono(di)ethanolamide, ethyleneglycol monoethylether, polyoxypropylene alkyl ether, polyglycerin alkyl ester, and alkyl sulphone.

Examples of the solubilizing agent and humectants are lanolin, olive oil, glycerin, benzyl alcohol, butyl benzoate, isopropyl myristate, octanol, 1,3-butyleneglycol, and (poly-)ethyleneglycol.

Furthermore, as optional ingredients, fillers, adhesive adds, and softening agents can be formulated, for example, to retain the form of a polymer substance layer.

Examples of the filler are silica, titanium dioxide, calcium carbonate, kaolin, mica, zinc oxide, aluminum hydroxide, barium sulfate, starch, talc, and clay. Examples of the adhesive aids are ethyl acetate, butyl acetate, triethyl citrate, and butyl alcohol. Examples of the softening agents are various plasticizers, polybutenes, polyisoprene having a low polymerization degree.

The tape or sheet for skin external application can be prepared in any conventional manner for preparing a pressure-sensitive adhesive tape or sheet. For example, the polyoxyalkylene-modified organopolysiloxane is dispersed in a polymer substance solution dissolved in a solvent, or in a polymer substance emulsion dispersed in an aqueous medium, followed by coating the resultant solution or emulsion on a substrate in the form of a sheet or tape. The tape or sheet is then dried to obtain the desired tape or sheet for skin external application. Alternatively, the polyoxyalkylene-modified organopolysiloxane can be coated or sprayed on the polymer substance layer previously formed on a substrate in the same manner as mentioned above. The coating may be carried out in any conventional manner including a spray coating, roll coating, gravure coating, reverse coating, dip coating, screen printing, or flexographic printing.

The drying of the coated film can be carried out in any conventional manner as long as the liquid component of the aqueous medium or the solvent in the polymer solution can be evaporated. For this purpose, the heating at a temperature of about 90° C. to 180° C. for about 1 to 10 minutes by a hot-air drying, an infrared ray heating, and a far infrared ray heating method can be adopted. Although the thickness of the polymer layer having pressure-sensitivity adhesion largely depends upon the type of the tape or sheet for skin external application, the thickness of 0.5 mm or less can be advantageously used in the case of adhesive tapes or straps and the thickness of 0.5 mm or more can be advantageously used in the case of plasters and cataplasms or poultices.

As the polymer substances, any conventional polymer substances having an adhesive property at room temperature usually used in the preparation of pressure-sensitive adhesive tapes. Examples of such polymer substances are acrylic polymers (e.g., homopolymers of acrylic or methacrylic esters or copolymers thereof with other polymerizable monomers including organic acids, esters, amides or vinyl monomers, elastomeric polymers, and vinyl polymers.

As the substrates, any conventional substrates or supports usable in the preparation of pressure-sensitive tapes or sheets, such as papers, woven or nonwoven fabrics, polymer films, celophanes, or metalic foils, or their laminates can be used in the present invention.

Adhesive Composition for False Eyelash

The present inventors have further found that an adhesive for a false eyelash having a strong adhesive force with a low skin irritation effect can be obtained by formulating a specific silicon compound of the organopolysiloxane type into an adhesive for a false eyelash, and the present invention was accomplished on the basis of this finding.

Thus, in accordance with the present invention, there is also provided an adhesive for a false eyelash, comprising a polyoxyalkylene-modified organopolysiloxane having the formula (A), (B), (C), or (D), a latex and/or a synthetic resin emulsion.

The polyoxyalkylene-modified organopolysiloxane used in an adhesive composition for a false eyelash according to the present invention preferably has an average molecular weight of 3000 or more, mere preferably 5000 to 50000. Also the polyoxyalkylene-modified organopolysiloxane preferably contains 2% to 80% by weight of polyoxyalkylene groups in the molecule, more preferably 11% to 50% by weight, to ensure that the desired effect is exhibited.

The amount of the polyoxyalkylene-modified organopolysiloxane formulated in the adhesive for a false eyelash may be 0.1% to 20% by weight, preferably 0.2% to 10% by weight. At an amount less than 0.1% by weight, skin irritation effect is not sufficiently reduced. On the other hand, if more than 20% by weight is used, the false eyelash is liable to fall oil.

As the adhesive to be used in the present invention, natural and synthetic latices, acrylic, vinyl acetate, styrene, olefin, alkyd type synthetic resin emulsions may be employed. Any one or two or more adhesives may be selected from thereamong. The amount formulated is preferably 10% to 90% by weight of an emulsion with a resin concentration of 50% by weight.

The adhesive for a false eyelash of the present invention can further formulate humectants, surfactants, preservatives, and the like, if desired, in addition to the above essential components. Of course, the above must be used under the qualitative and quantitative conditions which do not impair the object of the present invention.

Decolorant Composition

The present inventors have further found that the skin irritation effect is remarkably reduced by formulation of a specific silicon compound of the organopolysiloxane type having the formula (A), (B), (C), or (D) in a decolorant composition, without impairing the decoloration effect, and the present invention was accomplished on the basis of that finding.

Thus, in accordance with the present invention, there is further provided a decolorant composition for head hair and unnecessary hair on arms and legs comprising a polyoxyalkylene-modified organopolysiloxane having the above-mentioned formula (A), (B), (C), or (D).

The polyoxyalkylene-modified organopolysiloxane used in the decolorant composition of the present invention preferably has an average molecular weight of 3000 or more, more preferably 5000 to 50000. Also the polyoxyalkylene-modified organopolysiloxane preferably contains 2% to 80% by weight off polyoxyalkylene groups in the molecule, more preferably 11% to 50% by weight, to ensure that the desired effect is exhibited.

The amount of the polyoxyalkylene-modified organopolysiloxane formulated is preferably 0.1% to 40% by weight, more preferably 0.5% to 30% by weight, where the first agent and the second agent are mixed, in the total weight of the decolorant composition.

The decolorant composition of the present invention can further formulate humectants, surfactants, preservatives, and the like, if desired, in addition to the above essential components. Of course, the above must be used under the qualitative and quantitative conditions which do not impair the object of the present invention.

The decolorant for head hair and unnecessary hair on the legs and arms, containing the polyoxyalkylene-modified organopolysiloxane of the present invention, has the low skin irritation effect and a good decoloration effect.

Depilatory Composition

The present inventors have further found that skin irritation such as blisters, eruptions, and the like is remarkably reduced by the formulation of a specific organopolysiloxane type compound in a depilatory such as a depilatory wax, depilatory liquid, tape or sheet for depilation, and the like, and thus accomplished the present invention.

Thus, in accordance with the present invention, there is further provided a depilatory composition having a low skin irritation effect and an extremely high safety factor when used on the human body, comprising a polyoxyalkylene-modified organopolysiloxane having the above mentioned formula (A), (B), (C), or (D).

The polyoxyalkylene-modified organopolysiloxane in the present invention preferably has an average molecular weight of 3000 or more, more preferably 5000 to 50000. Also the polyoxyalkylene-modified organopolysiloxane preferably contains 2% to 80% by weight of polyoxyalkylene groups in the molecule, more preferably, 11% to 50% by weight, to ensure that the desired effect is exhibited.

The amount of the polyoxyalkylene-modified organopolysiloxane formulated in the depilatory base is preferably 0.1% to 50% by weight, more preferably 0.1% to 30% by weight.

The depilatory composition in which the alleviator of the present invention is to be formulated is not limited, and any desired form of depilatory base may be used.

In the depilatory composition of the present invention, depending on the type, there may be formulated components conventionally used for skin external preparations such as inorganic powder, organic powder, pigment, resin, mineral, oil component, water, surfactant, humectant, lower alcohol, tackifier, perfume, antioxidant, chelating agent, dye, preservative, antifungal agent, and the like.

Any desired dosage form of the depilatory of the present invention may be used, including a paste, solution system, soluble system, emulsion system, powder dispersion system, water-oil two layer system, water-oil-powder three layer system, and the like.

The depilatory composition of the present invention has a high skin safety factor and can be used without the formation of the red swellings or blisters on the skin that occur when a conventional depilatory is used.

Eyeliner Composition

The present inventors further found that an eyeliner composition capable of forming a firm film, having an excellent cosmetic preservation and low skin irritation effect can be obtained by formulating a specific organopolysiloxane compound into an eyeliner, and the present invention was accomplished on the basis of this finding.

Thus, in accordance with the present invention, there is further provided an eyeliner composition comprising a polyoxyalkylene-modified organopolysiloxane having the above-mentioned formula (A), (B), (C), or (D) and a synthetic resin emulsion.

The polyoxyalkylene-modified organopolysiloxane used in the present invention preferably has an average molecular weight of 3000 or more, more preferably 5000 to 50000. Also the polyoxyalkylene-modified organopolysiloxane preferably contains 2% to 80% by weight of polyoxyalkylene groups in the molecule, more preferably 11% to 50% by weight, to ensure that the required effect is exhibited.

The amount of the polyoxyalkylene-modified organopolysiloxane formulated in the eyeliner is preferably 0.1% to 20% by weight, more preferably 0.2% to 10% by weight. At an amount less than 0.1% by weight, the skin irritation effect is not sufficiently reduced. On the other hand, at an amount of more than 20% by weight, the film will be weakened, and thus the cosmetic preservation effect will be poor.

As the adhesive to be used in the present invention, acrylic, vinyl acetate, styrene, olefin, alkyd type synthetic resin emulsions may be employed. Any one or two or more adhesives may be selected therefrom., The amount formulated is preferably 5% to 70% by weight of an emulsion with a resin concentration of 50% by weight.

The eyeliner of the present invention can contain, in addition to the above essential components and, if desired, inorganic pigments, inorganic powders such as talc, kaolin, calcium carbonate, zinc white, titanium dioxide, red iron oxide, yellow iron oxide, black iron oxide, ultramarine, titanium-coated mica, bismuth oxychloride, blood red, caked pigment, ultramarine pink, chromium hydroxide, mica titanium, yellow iron oxide, chromium oxide, aluminum oxide, cobalt, Prussian blue, black iron oxide, carbon black, silicic anhydride, magnesium silicate, bentonite, mica, zirconium oxide, magnesium oxide, zinc oxide, titanium oxide, light calcium carbonate, heavy calcium carbonate, light magnesium carbonate, heavy magnesium carbonate, calamine, talc, titanium oxide, kaolin, silicic anhydride, silicate, zinc oxide, calcium carbonate, magnesium carbonate, red iron oxide, yellow iron oxide, chromium oxide, carbon black, Prussian blue, mica, cericite, nylon powder, polyethylene powder, cellulose powder, acrylic resin, titanium dioxide, iron oxide, and the like, or organic pigments oils and fats such as various lakes, and the like, perfumes, humectants, surfactants, preservatives, and the like. Note, the above must be used under the qualitative and quantitative conditions which do not impair the objects of the present invention.

EXAMPLES

The present invention will now be further illustrated by, but is by no means limited to, the following Examples, wherein all parts and percentages are expressed on a weight basis unless otherwise noted.

Example 1-1

Using a fluid paraffin and squalane as the hydrocarbon oil, and cetyl isooctanoate and glycerine tri-2-ethylhexanoate as the ester oil, a composition was prepared by formulating 50% of a polyoxyethylene-modified organopolysiloxane having the structure of formula (A), containing 20% of polyoxyethylene groups and having an average molecular weight of 6000 with these oil components, and open coating was performed on the skin of a guinea pig once per day for 3 days for an examination of the skin primary irritation value, to obtain the results shown in Table 1-1.

An evaluation of the skin primary irritation effect shows that irritation values of less than 0–2 denote no irritation, and irritation values of 2–4 denote irritation.

TABLE 1-1

| Oil component | Irritation value |
|---|---|
| Fluid paraffin | 1.6 (2.8)* |
| Squalane | 0.2 (1.0) |
| Cetyl isooctanoate | 1.5 (1.8) |
| Glycerine tri-2-ethylhexanoate | 1.0 (1.8) |

*The value in the bracket is the irritation value for a 100% oil component.

It can be seen from the results in Table 1-1 that each composition has an irritation value of less than 2, thus being free from skin irritation, and that the irritation effect of the respective oil components is reduced.

Example 1-2 and Comparative Example 1-1

Using a commercially available set of an acrylic tackifier and a hardening agent (Sibinol produced by Saiden Kagaku Co.), 80 parts of a tackifier and 20 parts of a hardening agent were mixed, and further, 4 parts of the same polyoxyethylene-modified organopolysiloxane used in Example 1-1 were mixed with these mixtures, and the resultant mixture was coated uniformly onto a sheet of a vinyl chloride resin to prepare a tacky tape of Example 1-2.

Similarly, a tacky tape of Comparative Example 1-1 was prepared as mentioned above, except that the polyoxyethylene-modified organopolysiloxane was not used.

The tapes having a size of 4 cm×7 cm were plastered onto the skin of a human forearm of persons easily subjected to eruption for 24 hours, and the skin irritation values were evaluated 2 hours, 5 hours, and 24 hours after peel-off of the tacky tape to obtain the results shown in Table 1-2. Evaluation of the skin irritation effect is evaluated as follows.

| No erythema | − |
|---|---|
| Slight erythema | ± |
| Erythema | + |
| Strong erythema | ++ |
| Strong erythema edema | +++ |

TABLE 1-2

| | Results after Peel-off of Tacky Tape | | | | | |
|---|---|---|---|---|---|---|
| | After 2 hrs | | After 5 hrs | | After 24 hrs | |
| Tested subject | Example | Com. Ex. | Example | Com. Ex. | Example | Com. Ex. |
| 1 | − | ± | − | ± | − | ± |
| 2 | − | ± | − | ± | −. | ± |
| 3 | ± | ± | − | ± | − | ± |
| 4 | − | ± | − | ± | − | ± |
| 5 | ± | + | − | + | − | + |
| 6 | − | + | − | + | − | ± |
| 7 | − | + | − | + | − | ± |
| 8 | ± | + | − | + | − | + |
| 9 | − | + | − | + | − | + |
| 10 | − | + | − | + | − | + |

From the results shown in Table 1-2, it can be understood that the skin irritation effect is low in each tested subject, and that skin irritation disappeared after a short time even in each tested subject who exhibited ± irritation value.

Furthermore, the glue remaining phenomenon on the released sheet and the skin surface applied was observed in Comparative Example 1-1, whereas such phenomenon was not observed and the retention force on the skin was good in Example 1-2. The retention force was determined whether or not an applied test sample having a size of 4 cm×7 cm is peeled off from the skin 24 hours after the sample was applied to the skin of a human forearm. Furthermore, the glue remaining phenomenon was determined whether or not the adhesives (i.e., glue) remains on the surface of a release sheet released from the tape when the tape is applied to a skin and also whether or not the glue remains on the skin when the tape is removed from the skin of a human forearm after 24 hr application.

Example 1-3 and Comparative Example 1-2

The polyoxyethylene-modified organopolysiloxane used in Example 1-1 was coated at a coverage of 120 g/m² on a commercially available adhesive plaster for a patch test (produced by Torii Seiyaku K. K.) to obtain an adhesive tape for skin external application (Example 1-3).

The above-mentioned commercially available adhesive plaster was used in Comparative Example 1-2.

The evaluation results of the skin irritation effects of the tapes of Example 1-3 and Comparative Example 1-2 are shown in Table 1-3. As is clear from the results shown in Table 1-3, the skin irritation effect was observed in Comparative Example 1-2, whereas no skin irritation effect was observed in Example 1-3. Thus, the tape according to the present invention is far safer to use because of the irritation effect.

Furthermore, the tape according to the present invention exhibited no glue remaining phenomenon and good retention force, whereas the glue remaining phenomenon was observed in Comparative Example 1-2.

TABLE 1-3

Skin Irritation Effect Evaluation Result

| Test Subject | After 2 hrs Ex. 1-3 | After 2 hrs Com. Ex. 1-2 | After 5 hrs Ex. 1-3 | After 5 hrs Com. Ex. 1-2 | After 24 hrs Ex. 1-3 | After 24 hrs Com. Ex. 1-2 |
|---|---|---|---|---|---|---|
| 1 | − | ± | − | ± | − | − |
| 2 | − | ± | − | ± | − | ± |
| 3 | ± | ± | − | ± | − | ± |
| 4 | − | ± | − | ± | − | − |
| 5 | ± | + | − | + | − | + |
| 6 | − | + | − | + | − | + |
| 7 | − | + | − | + | − | ± |
| 8 | ± | ± | − | ± | − | ± |
| 9 | − | + | − | + | − | + |
| 10 | − | + | − | + | − | ± |

Example 1-4

The external skin application tape was produced in the same manner as in Example 1-2, except that 45 parts of a polyoxyethylene-modified organopolysiloxane having a structure (B) and containing 75% of polyoxyethylene group and an average molecular weight of 30000 was used instead of 4 parts of the polyoxyethylene-modified organopolysiloxane used in Example 1-2.

Example 1-5

The external skin application tape was produced in the same manner as in Example 1-2 except that 0.5 part of a polyoxyethylene-modified organopolysiloxane having a structure (C) and containing 77% of polyoxyethylene group and an average molecular weight of 3000 was used instead of 4 parts of the polyoxyethylene-modified organopolysiloxane used in Example 1-2.

Example 1-6

The external skin application tape was produced in the same manner as in Example 1-2, except that 20 parts of a polyoxyethylene-modified organopolysiloxane having a structure (A) and containing 50% of polyoxyethylene group and an average molecular weight of 20000 was used instead of 4 parts of the polyoxyethylene-modified organopolysiloxane used in Example 1-2.

The results of the skin irritation effect evaluation after 2 hours from the application are shown in Table 1-4. As is clear from the results shown in Table 1-4, the skin irritation effects of the tapes of Example 1-4 to 1-6 were slight and these tapes have excellent safety. Furthermore, the tapes of Examples 1-4 to 1-6 have an excellent retention force and exhibit no substantial glue remaining phenomenon.

TABLE 1-4

Skin Irritation Effect Evaluation Result

| Test Subject | Example 1-4 | Example 1-5 | 1-6 |
|---|---|---|---|
| 1 | − | ± | ± |
| 2 | ± | ± | ± |
| 3 | ± | − | ± |
| 4 | − | ± | − |
| 5 | ± | ± | ± |
| 6 | ± | ± | ± |
| 7 | ± | − | − |
| 8 | ± | ± | ± |
| 9 | − | − | − |
| 10 | − | ± | − |

Example 1-7

A 6 part amount of the same polyoxyethylene-modified organopolysiloxane as used in Example 1-2 was mixed with 100 parts of a commercially available vinyl adhesive containing as a main component polyvinyl alcohol. The mixture was uniformly coated on a polyethylene film, followed by drying. Thus, the skin external application tape was obtained.

Comparative Example 1-3

The skin external application tape was produced in the same manner as in Example 1-7, except that the polyoxyethylene-modified organopolysiloxane was not formulated therein.

The results of the skin irritation effect evaluation after 2 hours from the application are shown in Table 1-5.

As is clear from the results shown in Table 1-5, the skin irritation effect of the tape of Example 1-7 was slight and the safety thereof was excellent, whereas skin irritation effects were observed in Comparative Example 1-3. Furthermore, the glue remaining phenomena on the release sheet and the skin surface applied was observed in Comparative Example 1-3, while as no such phenomenon was observed in Example 1-7. Moreover, the retention force of Example 1-7 was good.

TABLE 1-5

Skin Irritation Effect Evaluation Result

| Test Subject | Example 1-7 | Com. Example 1-3 |
|---|---|---|
| 1 | − | ± |
| 2 | − | ± |
| 3 | ± | + |
| 4 | ± | + |
| 5 | − | ± |
| 6 | − | ± |
| 7 | − | ± |
| 8 | − | + |
| 9 | ± | + |
| 10 | − | ± |

The skin external application tapes or sheets containing drugs are now explained hereinbelow. The release of the drug and the dissolution of the drug are determined as follows:

Determination of the Release of the Drug

A test sample of the skin external application tape having a size of 4 cm×7 cm was prepared and this sample was applied to the skin of a healthy person for a given time. After removing off, the amount of the drug remained in the tape was quantitatively determined to obtain the amount of the drug released from the adhesive layer.

Determination of the Dissolution of the Drug

After the skin external application tape or sheet was allowed to stand at room temperature for one month, the presence or absence of drug crystal was examined by a microscope.

Example 1-8

A 80 part amount of the adhesive used in Example 1-2 were thoroughly mixed with 6.9 parts of l-menthol, 4.9 parts of glycol salicylate, 0.018 parts of nonylic vanilyl amide and 5 parts of polyoxyethylene-modified organopolysiloxane having a structure of the formula (A) and an average molecular weight of 6000 and containing 20% of polyoxyethylene group. After the mixture was further mixed with 10 parts of a 30% aqueous solution of Hiviswako® 104 (i.e., carboxyvinyl polymer) and 20 parts of the curing agent used in Example 1-2, the mixture was uniformly coated on polyolefin non-woven fabric followed by drying. Thus, the desired skin external application tape was obtained.

Comparative Example 1-4

The skin external application tape was produced in the same manner as in Example 1-8, except that polyoxyethylene-modified organopolysiloxane was not used.

The results of the evaluation of the skin irritation effect are shown in Table 1-6.

As is clear from the results shown in Table 1-6, the skin irritation effects of the tape of Example 1-7 were slight in every test subject and the safety thereof was excellent, whereas the skin irritation effects were observed in Comparative Example 1-4. Furthermore, the glue remaining phenomena on the release sheet and the skin surface applied were not observed in Example 1-8, and the retention force of Example 1-8 was good.

Moreover, the release of the drug of Example 1-8 was good and the drug dissolubility was good (i.e., no crystallization was observed) in Example 1-8.

TABLE 1-6

| | Skin Irritation Effect Evaluation Result | | | | | |
|---|---|---|---|---|---|---|
| | After 2 hrs | | After 5 hrs | | Afer 24 hrs | |
| Test subject | Ex. 1-8 | Com. Ex. 1-4 | Ex. 1-8 | Com. Ex. 1-4 | Ex. 1-8 | Com. Ex. 1-4 |
| 1 | ± | ++ | ± | ++ | − | + |
| 2 | − | + | − | + | − | + |
| 3 | − | + | − | + | − | + |
| 4 | ± | ++ | ± | ++ | − | + |
| 5 | ± | + | − | ++ | − | + |
| 6 | − | ++ | − | + | − | ± |
| 7 | ± | ++ | ± | ++ | − | + |
| 8 | ± | ++ | − | ++ | − | + |
| 9 | ± | ++ | ± | ++ | − | + |
| 10 | − | + | − | + | − | ± |

Example 1-9 and Comparative Example 1-5

The skin application tape of Example 1-9 was prepared by coating 120 g/m² of the polyoxyethylene-modified organopolysiloxane used in Example 1-8 on a commercially available antiphlogistic and analgesic plaster. This commercially available plaster was evaluated as Comparative Example 1-5.

The results are shown in Table 1-7.

As is clear from the results shown in Table 1-7, the skin irritation effect of the tape of Example 1-9 was slight and the safety thereof was excellent, whereas the skin irritation effect was observed in the commercially available plaster of Comparative Example 1-5. Furthermore, the glue remaining phenomena on the release sheet and the skin surface applied was observed in Comparative Example 1-5.

TABLE 1-7

| | Skin Irritation Effect Evaluation Result | | | | | |
|---|---|---|---|---|---|---|
| | After 2 hrs | | After 5 hrs | | Afer 24 hrs | |
| Test subject | Ex. 1-9 | Com. Ex. 1-5 | Ex. 1-9 | Com. Ex. 1-5 | Ex. 1-9 | Com. Ex. 1-5 |
| 1 | − | + | − | + | − | + |
| 2 | ± | ± | ± | ± | − | ± |
| 3 | − | ± | ± | + | − | ± |
| 4 | ± | + | − | + | − | + |
| 5 | ± | ++ | ± | ++ | − | + |
| 6 | ± | + | − | + | − | + |
| 7 | ± | ++ | ± | ++ | − | ++ |
| 8 | ± | + | ± | + | − | + |
| 9 | − | + | − | + | − | ± |
| 10 | ± | + | − | + | − | + |

Example 1-10

A 80 part amount of the adhesive and 20 parts of the curing agent used in Example 1-8 were thoroughly mixed with 9.5 parts of l-menthol, 6.8 parts of glycol salicylate, 0.024 parts of nonylic vanilyl amide and 45 parts of polyoxyethylene-modified organopolysiloxane having a structure of the formula (B) and an average molecular weight of 30000 and containing 75% of polyoxyethylene group. The mixture was uniformly coated on polyolefin non-woven fabric used in Example 1-8, followed by drying. Thus, the desired skin external application tape was obtained.

Example 1-11

A 80 part amount of the adhesive and 20 parts of the curing agent used in Example 1-8 were thoroughly mixed with 6.6 parts of l-menthol, 4.7 parts of glycol salicylate, 0.017 parts of nonylic vanilyl amide and 0.5 parts of polyoxyethylene-modified organopolysiloxane having a structure of the formula (C) and an average molecular weight of 3000 and containing 11% of polyoxyethylene group. The mixture was uniformly coated on polyolefin non-woven fabric used in Example 1-8, followed by drying. Thus, the desired skin external application tape was obtained.

Example 1-12

A 80 part amount of the adhesive and 20 parts of the curing agent used in Example 1-8 were thoroughly mixed with 13.1 parts of l-menthol, 9.3 parts of glycol salicylate, 0.033 parts of nonylic vanilyl amide and 100 parts of polyoxyethylene-modified organopolysiloxane having a structure of the formula (A) and an average molecular weight of 20000 and containing 50% of polyoxyethylene group. The mixture was uniformly coated on polyolefin non-woven sheet used in Example 1-8, followed by drying. Thus, the desired skin external application tape was obtained.

The results of the skin irritation effect evaluation of the tapes of Examples 1-10 to 1-12 after 2 hours from the applications are shown in Table 1-8.

As is clear from the results shown in Table 1-8, the skin irritation effects of these tapes were slight and the safety thereof was excellent. Furthermore, the tapes of Examples 1-10 to 1-12 had a good retention force, as well as good drug release and good dissolution of the drug. Additionally said tapes exhibited no substantial glue remaining phenomenon.

TABLE 1-8

| Skin Irritation Effect Evaluation Result (After 2 hrs) | | | |
|---|---|---|---|
| Test subject | Example 1-10 | Example 1-11 | Example 1-12 |
| 1 | ± | ± | ± |
| 2 | ± | ± | ± |
| 3 | ± | ± | ± |
| 4 | − | ± | ± |
| 5 | ± | ± | − |
| 6 | ± | ± | ± |
| 7 | ± | ± | ± |
| 8 | ± | ± | ± |
| 9 | ± | ± | − |
| 10 | − | ± | ± |

Example 1-13

To 100 parts of a commercially available vinyl tape adhesive containing polyvinyl alcohol as a main component, 11.7 parts of l-menthol, 12.4 parts of methyl salicylate, 0.5 parts of mentha oil, 2.0 parts of dl-camphor, 0.5 parts of thymol, 0.3 parts of tocopherol acetate, 3.4 parts of glycol salicylate, and 6 parts of the polyoxyethylene-modified organopolysiloxane used in Example 1-8 were addred, followed by thoroughly mixing. The resultant mixture was uniformly coated on a polyolefin non-woven fabric. After drying, the desired skin external application tape was obtained.

Comparative Example 1-6

The skin external application tape was produced in the same manner as in Example 1-13 except that the polyethylene-modified organopolysiloxane was not used.

The evaluation results of the skin irritation effects of the tapes of Example 1-13 and Comparative Example 1-6 are shown in Table 1-9. As is clear from the results shown in Table 1-9, the skin irritation effect (after 2 hrs) was observed in Comparative Example 1-6, whereas no skin irritation effect was observed in Example 1-13. Thus, the tape according to the present invention are far safer to use.

Furthermore, the tapes of Example 1-13 had a good retention force, as well as good drug release and good dissolution of the drug. Additionally, said tapes exhibited no substantial glue remaining phenomenon.

TABLE 1-9

| Skin Irritation Effect Evaluation Result (After 2 hrs) | | |
|---|---|---|
| Test subject | Example 1-13 | Comparative Example 1-6 |
| 1 | − | + |
| 2 | − | + |
| 3 | ± | ++ |
| 4 | ± | ++ |

TABLE 1-9-continued

| Skin Irritation Effect Evaluation Result (After 2 hrs) | | |
|---|---|---|
| Test subject | Example 1-13 | Comparative Example 1-6 |
| 5 | ± | ++ |
| 6 | ± | ++ |
| 7 | − | ++ |
| 8 | ± | ++ |
| 9 | ± | ++ |
| 10 | − | + |

Example 1-14

To 100 parts of a commercially available vinyl type adhesive containing polyvinyl alcohol as a main component used in Example 1-13, 11.7 parts of l-menthol, 12.4 parts of methyl salicylate, 0.5 parts of mentha oil, 2.0 parts of dl-camphor, 0.5 parts of thymol, 0.3 parts of tocopherol acetate, 3 parts of glycol salicylate, 3 parts of the polyoxyethylene-modified organopolysiloxane used in Example 1-8, and 3 parts polyoxyethylene-modified organopolysiloxane used in Example 1-10 were added, followed by thoroughly mixing. The resultant mixture was uniformly coated on a polyolefin non-woven fabric. After drying, the desired skin external application tape was obtained.

Comparative Example 1-7

The skin external application tape was produced in the same manner as in Example 1-14 except that the polyoxyethylene-modified organopolysiloxanes were not used.

The evaluation results of the skin irritation effects of the tapes of Example 1-14 and Comparative Example 1-6 are shown in Table 1-10. As is clear from the results shown in Table 1-10, the skin irritation effect (after 2 hours) was observed in Comparative Example 1-7, whereas no skin irritation effect was observed in Example 1-10. Thus, the tape according to the present invention is far safer to use.

Furthermore, the tapes of Example 1-14 had a good retention force, as well as good drug release and good dissolution of the drug. Also, said tapes exhibited no substantial glue remaining phenomenon.

TABLE 1-10

| Skin Irritation Effect Evaluation Result (After 2 hrs) | | |
|---|---|---|
| Test subject | Example 1-14 | Comparative Example 1-7 |
| 1 | ± | ++ |
| 2 | − | ++ |
| 3 | ± | ++ |
| 4 | ± | + |
| 5 | − | ++ |
| 6 | ± | ++ |
| 7 | − | + |
| 8 | ± | ++ |
| 9 | ± | + |
| 10 | − | ++ |

The tape or sheet for skin external application use according to the present invention is far safer. Additionally said tape possess an excellent adhesion property, and glue remaining property, as well as excellent dissolution of the drug and excellent release of the drug.

Example 2-1

As the alleviator of the present invention, a polyoxyethylene-modified organopolysiloxane having the structure of the formula (A), containing 20% of intramolecular polyoxyethylene groups and having an average molecular weight of 6000 was used, and as Comparative Examples, a polyoxyethylene-modified organopolysiloxane having the structure of the formula (A), containing 20% of polyoxyethylene groups in the molecule and having an average molecular weight of 3000, diglycerine diisostearate and sorbitan monoisostearate were used, and 50% compositions of these with the same four kinds of oil components as used in Example 1-1 were prepared and skin irritation tests were conducted for an examination of the irritation effect.

The results are shown in Table 2-1

SKIN IRRITATION PER TEST OF EXAMPLE 1-1

TABLE 2-1

| Oil component | Alleviator | | | |
|---|---|---|---|---|
| | (1) | (2) | (3) | (4) |
| Fluid paraffin | 1.6 | 3.1 | 2.8 | 2.8 |
| Squalane | 0.2 | 0.8 | 2.7 | 2.7 |
| Cetyl isooctanoate | 1.5 | 2.7 | 2.7 | 2.7 |
| Glycerine tri-2-ethylhexanoate | 1.0 | 2.7 | 3.2 | 3.3 |

(1): Formula (I): 20% of polyoxyethylene groups; average molecular weight 6000
(2): Formula (I): 20% of polyoxyethylene groups; average molecular weight 3000
(3): Diglycerine diisostearate
(4): Sorbitan monoisostearate From the results in Table 2-1, it can be understood that the polyoxyethylene-modified organopolysiloxane of the present invention shows no skin irritation effect and has an excellent safety factor, in contrast to the polyoxyethylene-modified organosiloxane with an average molecular weight of 3000, diglycerine diisostearate and sorbitan monoisostearate which increase the skin irritation effect of oil components.

Example 2-2

Emulsified compositions with the recipes shown in Table 2-2 were prepared.

TABLE 2-2

| | Example | Comparative Example |
|---|---|---|
| Cetyl isooctanoate | 50 | 50 |
| Formula (I): | | |
| 40% polyoxyethylene groups; average molecular weight 20000 | 3 | — |
| Diglycerine diisostearate | — | 3 |
| Purified water | 47 | 47 |

These emulsified compositions were examined to determine the skin irritation effect thereof according to the same method as in Example 1-1 to obtain the results shown in Table 2-3.

SKIN IRRITATION PER TEST OF EXAMPLE 1-1

TABLE 2-3

| | Example | Comparative Example |
|---|---|---|
| Skin irritation | 1.0 | 2.0 |

From the results in Table 2-3, it can be understood that the emulsified composition of Example shows no irritation effect, thus proving that the surfactant of the present invention has an excellent safety factor without skin irritation.

Examples 3-1 to 3-4 and Comparative Examples 3-1 and 3-2

Adhesives for a false eyelash with the following compositions were prepared for an investigation of the skin irritation effects thereof.

| Composition | |
|---|---|
| Polyoxyalkylene-modified organopolysiloxane (Table 3-1) | 5.0 |
| Milk casein | 2.0 |
| Deionized water | 22.7 |
| Natural latex | 70.0 |
| Methyl paraben | 0.3 |

The skin irritation effect was evaluated according to the method as shown below. The results are shown in Table 3-1.

Skin Irritation Test and Evaluation Method

The hair on the back of a guinea pig weighing 300 to 500 g was shaved by an electric clipper, and 0.3 ml of a sample was applied uniformly over an area of 3×4 cm.

For 3 guinea pigs, open coating was performed once per day for 3 days for an examination of the skin irritation effect. The results are shown in Table 3-1.

Judgement

A judgement of the skin irritation effect was conducted according to the judgement standards shown below, and the judgement was conducted with the naked eye.

| Judgement Standards | |
|---|---|
| Reaction | Evaluation Value |
| No change | 0 |
| Slight erythema | 1 |
| Erythema | 2 |
| Strong erythema or slight edema | 3 |
| Edema or further change | 4 |

From this judgement, the evaluation value is calculated based on the following formula.

$$\text{evaluation value} = \frac{\text{Total of the reaction evaluation points}}{3 \text{ (guinea pigs)} \times 3 \text{ (judgement days)}}$$

The skin irritation effect is evaluated from the evaluation value.

| Skin Irritation Effect Evaluation Standards | |
| --- | --- |
| Evaluation Value | Skin Irritation Effect Evaluation |
| 0–2.0 | Substantially no skin irritation |
| 2.1–4.0 | Skin irritation |

TABLE 3-1

| | Polyoxyalkylene-modified organosiloxane | evaluation point |
| --- | --- | --- |
| Example 3-1 | Formula (A) 20% polyoxyethylene groups; M.W. 6000 | 1.0 |
| Example 3-2 | Formula (A) 40% polyoxyethylene groups; M.W. 20000 | 0.8 |
| Example 3-3 | Formula (B) 60% polyoxyethylene groups; M.W. 10000 | 1.1 |
| Example 3-4 | Formula (C) 20% polyoxyethylene groups, 10% poly-oxypropylene groups; M.W. 4000 | 1.5 |
| Comparative Example 3-2 | None | 3.2 |

From the results in Table 3-1, it can be understood that the adhesives for the false eyelashes of Examples 3-1 to 3-4 of the present invention have a low skin irritation effect and an excellent safety factor.

Also, the products of the present invention of Examples 3-1 to 3-4 exhibited a good adhesive force as the adhesive for false eyelash.

Example 3-5 and Comparative Example 3-2

Adhesives for a false eyelash with the following compositions were prepared and the skin irritation effects thereof were investigated.

| | Example 3-5 | Comparative Example 3-2 |
| --- | --- | --- |
| Polyoxyalkylene-modified organosiloxane: | | |
| Formula (D) 50% polyoxyethylene groups M.W. 15000 | 3.0 | — |
| Polyoxyethylene (20 mole addition) lauryl ether | — | 3.0 |
| Synthetic latex | 64.7 | 64.7 |
| Polyethyl acrylate emulsion (50%) | 20.0 | 20.0 |
| Deionized water | 10.0 | 10.0 |
| 1,3-Butylene glycol | 2.0 | 0.3 |
| Methyl paraben | 0.3 | 0.3 |

An evaluation of the irritation effect was made according to the method shown below, when used by 20 healthy women. The results are shown in Table 3-2.

Skin Irritation Effect Test Method

Using a commercially available sticking plaster for a patch test, 0.05 ml of a substance to be tested was added dropwise on the lint. After the dropwise addition, the lint was stuck immediately onto the forearm and further fixed with an elastic bandage. After 24 hours, the sticking plaster was removed, and the skin reaction observed according to the following judgement standards.

| Judgement Standards | |
| --- | --- |
| Negative (−) | No reaction |
| Pseudo-positive (±) | Slight erythema |
| Weakly positive (+) | Erythema |
| Moderately positive (++) | Erythema, edema, papula |
| Strongly positive (+++) | Small blister, papula, edema |
| Most strongly positive (++++) | Excoriation, necrosis |

TABLE 3-2

| Judgement | Example 3-5 | Comparative Exampl 3-2 |
| --- | --- | --- |
| (−) | 18 | 7 |
| (±) | 2 | 8 |
| (+) | 0 | 4 |
| (++) | 0 | 1 |
| (+++) | 0 | 0 |
| (++++) | 0 | 0 |

From the results shown in Table 3-2, the present product of Example 3-5 was found to have a low skin irritation effect.

Also, the present product of Example 3-5 exhibited a good adhesive force as the adhesive for a false eyelash.

Examples 4-1 to 4-4 and Comparative Examples
4-1 and 4-2

Decolorant compositions with the following compositions were prepared for an investigation of the skin irritation effect thereof. The results are shown in Table 4-1.

| Composition | |
| --- | --- |
| First agent | |
| Polyoxyalkylene-modified organopolysiloxane (Table 4-1) | 20.0 |
| Oleic acid | 12.0 |
| Polyoxyethylene (2 mole addition) | 22.7 |
| Oleyl ether | 12.0 |
| Propylene glycol | 10.0 |
| Fluid paraffin | 10.0 |
| Ethanol | 5.0 |
| Sodium edetate | 0.5 |
| Perfume | 0.1 |
| Ammonia water | controlled to pH 10 |
| Purified water | balance |
| Second agent | |
| Aqueous hydrogen peroxide (30%) | 20.0 |
| Phosphate buffer | controlled to pH 4 |
| Purified water | balance |

Skin Irritation Test and Evaluation Method

The hair on the back of a guinea pig weighing 300 to 500 g was shaved by an electric clipper, and 0.3 ml of a sample was applied uniformly over an area of 3×4 cm.

For 3 guinea pigs, open coating was performed once per day for 3 days for a determination of the skin irritation effect. The results are shown in Table 4-1.

Judgement

Judgement of the skin irritation effect was conducted according to the standards shown below, and the judgement was conducted with the naked eye.

Judgement Standards

| Reaction | Evaluation point |
| --- | --- |
| No change | 0 |
| Slight erythema | 1 |
| Erythema | 2 |
| Strong erythema or slight edema | 3 |
| Edema or further change | 4 |

From this judgement, the evaluation value is calculated based on the following formula.

$$\text{Evaluation value} = \frac{\text{Total of reaction evaluation}}{3 \text{ (guinea pigs)} \times 3 \text{ (judgement days)}}$$

The skin irritation effect was evaluated from the evaluation value.

Skin Irritation Effect Evaluation Standards

| Evaluation value | Skin irritation effect evaluation |
| --- | --- |
| 0–2.0 | Substantially no skin irritation |
| 2.1–4.0 | Skin irritation |

TABLE 4-1

| | Polyoxyalkylene-modified organosiloxane | Evaluation value |
| --- | --- | --- |
| Example 4-1 | Formula (A) 20% polyoxyethylene groups; M.W. 6000 | 1.9 |
| Example 4-2 | Formula (A) 40% polyoxyethylene groups; M.W. 20000 | 2.0 |
| Example 4-3 | Formula (B) 60% polyoxyethylene groups; M.W. 10000 | 1.8 |
| Example 4-4 | Formula (C) 20% polyoxyethylene groups, 10% polyoxypropylene groups; M.W. 6000 | 1.9 |
| Comparative Example 4-1 | Formula (A) 20% polyoxyethylene groups; M.W. 2500 | 4.0 |
| Comparative Example 4-2 | None | 3.8 |

From the results in Table 4-1, it can be understood that the decolorant compositions of Examples 4-1 to 4-4 of the present invention have a low skin irritation effect and an excellent safety factor.

Also, in the decoloration power test using a strand of black hair, all of the decolorants formulated with the present products in Table 4-1 exhibited good decoloration power.

Example 4-5: Decolorant

A decolorant with the following composition was prepared.

| First agent | |
| --- | --- |
| Polyoxyalkylene-modified organosiloxane [Formula (D); 20% of polyoxyethylene groups; M.W. 6000] | 2.0 |
| Cetanol | 6.0 |
| Stearic acid | 2.0 |
| Fluid paraffin | 10.0 |
| Polyoxyethylene cetyl ether | 5.0 |
| Sodium lauryl sulfate | 2.0 |
| Propylene glycol | 5.0 |
| Ammonia | controlled to pH 10 |
| Perfume | 0.1 |
| Purified water | balance |

Second agent
The same as in Example 4-1

Comparative Example 4-3

A decolorant was prepared according to the same recipe as in Example 4-5, except for omitting the polyoxyalkylene-modified organosiloxane from Example 4-5.

The decolorants obtained in Example 4-5 and Comparative Example 4-3 were examined to determine the skin irritation effect. The results are shown in Table 4-2.

SKIN IRRITATION PER TEST OF EXAMPLE 4-1

TABLE 4-2

| | Example 5 | Comparative Example 3 |
| --- | --- | --- |
| Skin irritation | 1.0 | 3.0 |

Also, by use of the decolorant of Example 4-5, a 10 women having a surplus of unnecessary hair, coated the decolorant on their arms and legs, and washed the coating away about 10 minutes later. As the result, the women found that there was no stimulative feeling, and no rubor, eruption or edema. Also, black hair was found to be sufficiently decolored.

Example 5-1: Depilatory

| Ingredient | % |
| --- | --- |
| (1) Strontium sulfide | 40.0 |
| (2) Polyoxyalkylene-modified organopolysiloxane of the Formula (A) (polyoxyethylene groups 20%; M.W. 6000) | 5.0 |
| (3) Triethanolamine | 12.5 |
| (4) Glycerine | 12.5 |
| (5) Starch | 4.0 |
| (6) Gum tragacanth | 1.5 |
| (7) Magnesium carbonate | 1.2 |
| (8) Zinc white | 4.0 |
| (9) Water | 18.3 |
| (10) Perfume | 1.0 |

Comparative Example 5-1

Except for omitting the polyoxyalkylene-modified organopolysiloxane of (2) from Example 5-1 (replaced with water), Example 5-1 was wholly repeated to obtain Comparative Example 5-1.

The depilatories of Example 5-1 and Comparative Example 5-1 were applied openly on the skin of a guinea pig once per day for 3 days, for a determination of the skin primary irritation value.

Example 5-2

| Ingredient | % |
|---|---|
| (1) Calcium thioglycolate | 6.0 |
| (2) Polyoxyalkylene-modified organopolysiloxane of the formula (A) (polyoxyethylene groups 40%; M.W. 20000) | 3.0 |
| (3) Sodium lauryl sulfate | 0.5 |
| (4) Calcium hydroxide | 1.5 |
| (5) Cetanol | 5.0 |
| (6) Polyethylene glycol (M.W. 6000) | 3.0 |
| (7) Calcium carbonate | 21.5 |
| (8) Perfume | 0.15 |
| (9) Purified water | balance |

Preparation method

The above-mentioned ingredients (2), (3), (5), (6) and (8) were mixed and dissolved, and the solution was mixed under stirring into the mixture of the ingredients (1), (4), (7) and (9) to form a paste. The paste was thoroughly mixed by a homogenizer, then cooled to room temperature by a heat exchanger to obtain a depilatory cream.

Example 5-3

| Ingredient | % |
|---|---|
| (1) Calcium thioglycolate | 8.0 |
| (2) Calcium hydroxide | 8.0 |
| (3) Precipitated calcium carbonate | 13.0 |
| (4) Polyoxyalkylene-modified organopolysiloxane of the Formula (B) (polyoxyethylene groups 60%, average molecular weight 10000) | 10.0 |
| (5) Cetanol | 6.0 |
| (6) Polyoxyethylene stearic acid ether (E.O. 20 moles added) | 6.0 |
| (7) Perfume | 0.5 |
| (8) Purified water | balance |

Preparation method

After mixing the ingredients (1)–(3) and (8) at room temperature, the mixture was heated to 70° C., in which the mixture of ingredients (4)–(7) dissolved by mixing at 70° C. was added, followed by cooling to room temperature to obtain a cream-like depilatory.

Example 5-4: Depilatory Wax

| Ingredient | % |
|---|---|
| (1) Rosin | 58.0 |
| (2) Polyoxyalkylene-modified organopolysiloxane of the Formula (C) (polyoxyethylene groups 20%; polyoxypropylene groups 10%; average molecular weight 4000) | 25.0 |
| (3) Solid paraffin 60 | 2.0 |
| (4) Beeswax | 2.0 |

Example 5-4: Depilatory Wax -continued

| Ingredient | % |
|---|---|
| (5) Carnauba wax | 2.0 |
| (6) Candellila wax | 3.0 |
| (7) Titanium dioxide | 8.0 |
| (8) Perfume | q.s. |

Preparation method

The ingredients (1)–(8) were dissolved by mixing, and the mixture was cast into a mold and left to cool to room temperature to obtain a depilatory wax.

Comparative Example 5-2

| Ingredient | % |
|---|---|
| (1) Rosin | 83.0 |
| (2) Solid paraffin 60 | 2.0 |
| (3) Beeswax | 2.0 |
| (4) Carunauba wax | 2.0 |
| (5) Canderilla wax | 3.0 |
| (6) Titanium dioxide | 8.0 |
| (7) Perfume | q.s. |

Preparation method

The ingredients (1)–(8) were dissolved by mixing, and the mixture was cast into a mold and left to cool to room temperature to obtain a depilatory wax.

Example 5-5: Depilatory Lotion

| Ingredient | % |
|---|---|
| (1) Calcium thioglycolate | 7.0 |
| (2) Strontium hydroxide | 6.0 |
| (3) Sodium sulfide | 1.5 |
| (4) Polyoxyalkylene-modified organopolysiloxane of the Formula (D) (polyoxyethylene groups 50%; average molecular weight 15000) | 5.0 |
| (5) Perfume | 0.2 |
| (6) Purified water | balance |

Comparative Examples 5-3, 5-4, and 5-5

The silicon surfactants in Examples 5-2, 5-3, and 5-5 were removed and replaced with purified water to prepare depilatories of Comparative Examples 5-3, 5-4, and 5-5, respectively.

For the above depilatories, safety tests were conducted by using guinea pigs, to obtain the results as shown in Table 5-1.

SKIN IRRITATION PER TEST OF EXAMPLE 4-1

TABLE 5-1

| Example: | 5-1 | 5-2 | 5-3 | 5-4 | 5-5 |
|---|---|---|---|---|---|
| Skin primary irritation effect | 1.5 | 1.0 | 0.9 | 1.7 | 1.0 |

TABLE 5-1-continued

| Comparative Example: | 5-1 | 5-2 | 5-3 | 5-4 | 5-5 |
|---|---|---|---|---|---|
| Skin primary irritation effect | 3.6 | 3.1 | 2.5 | 2.4 | 2.8 |

Evaluation of the skin primary irritation effect shows that the irritation value of 0- less than 2 denotes substantially no irritation, and that of 2-4 denotes that irritation is felt.

Examples 6-1-6-4, Comparative Examples 6-1

Eyeliners with the following compositions were prepared and the skin irritation effect thereof investigated.

| Composition | |
|---|---|
| Ingredient | % |
| Polyoxyalkylene-modified organopolysiloxane (Table 1) | 5.0 |
| Bentonite | 2.0 |
| Deionized water | 37.4 |
| 1,3-Butylene glycol | 5.0 |
| Synthetic resin emulsion (Ethyl acrylate/methyl methacrylate = 10/90; resin conc. = 50%) | 40.0 |
| Black iron oxide | 10.0 |
| Polyoxyethylene sorbitan monolaurate | 0.3 |
| Methylparaben | 0.3 |

The skin irritation effect was evaluated according to the method as shown below. The results are shown in Table 6-1.
Skin Irritation Effect Test and Evaluation Method The hair on the back of a guinea pig weighing 300 to 500 g was shaved by an electric clipper, and 0.3 ml of a sample was applied uniformly over an area of 3 ×4 cm.

For 3 guinea pigs, open coating was performed once per day for 3 days, for an examination of skin irritation. The results are shown in Table 6-1.
Judgement The judgement of the skin irritation effect was conducted according to the judgement standards shown below, and was conducted with the naked eye.

| Judgement Standards | |
|---|---|
| Reaction | Evaluation |
| No change | 0 |
| Slight erythema | 1 |
| Erythema | 2 |
| Strong erythema or slight edema | 3 |
| Edema or further change | 4 |

From this judgement, the evaluation value is calculated based on the following formula.

$$\text{Evaluation value} = \frac{\text{Total of reaction evaluation}}{3 \text{ (guinea pigs)} \times 3 \text{ (judgement days)}}$$

The skin irritation effect is obtained from the evaluation value.

| Evaluation value | Skin Irritation Effect |
|---|---|
| 0–2.0 | Substantially no skin irritation |
| 2.1–4.0 | Skin irritation |

TABLE 6-1

| | Polyoxyalkylene-modified Organosiloxane | Evaluation value |
|---|---|---|
| Example 6-1 | Formula (A) 20% polyoxyethylene groups; M.W. 6000 | 0.5 |
| Example 6-2 | Formula (A) 40% polyoxyethylene groups; M.W. 20000 | 0.3 |
| Example 6-3 | Formula (B) 60% polyoxyethylene groups; M.W. 10000 | 0.9 |
| Example 6-4 | Formula (C) 20% polyoxyethylene groups, 10% polyoxypropylene groups; | 1.3 |
| Comparative Example 6-1 | None | 3.0 |

From the results in Table 6-1, it can be understood that the eyeliners of Examples 6-1 to 6-4 of the present invention have a low skin irritation effect, and thus an excellent safety factor.

Also, the products of the present invention of Examples 6-1–6-4 exhibited a good cosmetic preservation.

Example 6-5 and Comparative Example 6-2

Eyeliners with the following compositions were prepared, and the skin irritation effect thereof was investigated.

| | Example 6-5 | Comparative Example 6-2 |
|---|---|---|
| Polyoxyalkylene-modified organosiloxane: | | |
| Formula (D) 50% polyoxyethylene groups M.W. 15000 | 3.0 | — |
| Polyoxyethylene (20 mols addition) lauryl ether | — | 3.0 |
| Synthetic resin emulsion (Styrene/butyl acrylate = 30/70; resin conc. = 50%) | 20.0 | 20.0 |
| Deionized water | 49.4 | 49.4 |
| Ultramarine | 10.0 | 10.0 |
| Squalene | 3.0 | 3.0 |
| Bentonite | 1.0 | 1.0 |
| Xanthane gum | 0.3 | 0.3 |
| Glycerine | 3.0 | 3.0 |
| Methyl paraben | 0.3 | 0.3 |

An evaluation of the low irritation effect was made according to the method shown below, when used by 20 healthy women. The results are shown in Table 6-2.
Skin Irritation Test Method Using a commercially available sticking plaster for a patch test, 0.05 ml of a substance to be tested was added dropwise on the lint. After the dropwise addition, the lint was stuck immediately to the forearm and further fixed with an elastic bandage. After 24 hours, the sticking plaster was removed, and the skin reaction observed according to the following judgement standards.

| Judgement Standards | |
|---|---|
| Negative (−) | No reaction |
| Pseudo-positive (±) | Slight erythema |
| Weakly positive (+) | Erythema |
| Moderately positive (++) | Erythema, edema, papula |
| Strongly positive (+++) | Small blister, papula, edema |
| Most strongly positive (++++) | Excoriation, necrosis |

TABLE 6-2

| Judgement | Example 6-5 | Comparative Example 6-2 |
|---|---|---|
| (−) | 19 | 11 |
| (±) | 1 | 6 |
| (+) | 0 | 2 |
| (++) | 0 | 1 |
| (+++) | 0 | 0 |
| (++++) | 0 | 0 |

From the results shown in Table 6-2, the present product of Example 6-5 was found to have a low skin irritation effect.

Also, the present product of Example 6-5 exhibited good cosmetic preservation as an eye liner.

We claim:

1. In the application to the skin of a tacky tape or sheet with attendant skin irritation, the method of alleviating such skin irritation which comprises employing as said tacky tape or sheet one comprising a tacky layer having incorporated therein a skin irritation alleviation agent consisting essentially of 0.1 to 90% by weight of a polyoxyalkylene-modified organopolysiloxane having an average molecular weight of 3000 or more and having the formula (A), (B), (C), or (D):

$$\text{R}-\underset{\text{R}}{\overset{\text{R}}{\text{SiO}}}-\left[\underset{\text{R}}{\overset{\text{R}}{\text{SiO}}}\right]_m-\left[\underset{(CH_2)_pO(C_3H_6O)_y(C_2H_4O)_xR'}{\overset{\text{R}}{\text{SiO}}}\right]_n-\underset{\text{R}}{\overset{\text{R}}{\text{Si}}}-\text{R} \quad (A)$$

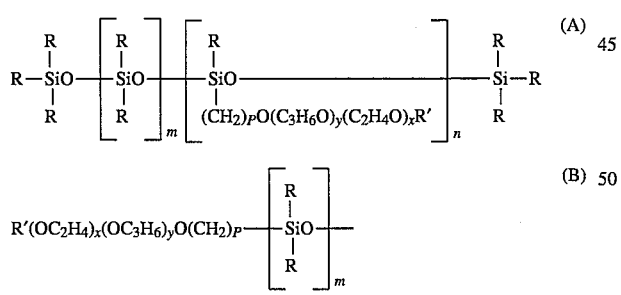

$$-\underset{\text{R}}{\overset{\text{R}}{\text{Si}}}-(CH_2)_pO(C_3H_6O)_y(C_2H_4O)_xR'$$

$$R'(OC_2H_4)_x(OC_3H_6)_yO(CH_2)_p-\left[\underset{\text{R}}{\overset{\text{R}}{\text{SiO}}}\right]_m \quad (C)$$

$$-\underset{\text{R}}{\overset{\text{R}}{\text{Si}}}-(CH_2)_pO(C_3H_6O)_y(C_2H_4O)_xR'$$

$$R-\underset{\text{R}}{\overset{\text{R}}{\text{SiO}}}-\left[\underset{\text{R}}{\overset{\text{R}}{\text{SiO}}}\right]_m-\left[\underset{(CH_2)_pO(C_3H_6O)_y(C_2H_4O)_xR'}{\overset{\text{R}}{\text{SiO}}}\right]_t \quad (D)$$

$$-\underset{\text{R}}{\overset{\text{R}}{\text{Si}}}-(CH_2)_pO(C_3H_6O)_y(C_2H_4O)_xR'$$

wherein R is an alkyl group having 1 to 3 carbon atoms or phenyl, R' is hydrogen or an alkyl group having 1 to 12 carbon atoms, p is an integer of 1 to 5, m is an integer of 5 to 100, n and x are each an integer of 1 to 50, and t and y are each an integer of 0 to 50.

2. A method as claimed in claim 1, wherein the amount of the polyoxyalkylene group in the polyoxyalkylene-modified organopolysiloxane molecule is 2% to 80% by weight.

3. A method as claimed in claim 1, wherein the amount of the polyoxyalkylene-modified organopolysiloxane in the tacky layer is 0.1% to 20% by weight.

4. A method as claimed in claim 1, wherein the amount of the polyoxyalkylene group in the polyoxyalkylene-modified organopolysiloxane molecule is 11% to 50% by weight and the molecular weight of such molecule is 5000 to 50000.

* * * * *